(12) United States Patent
Sinha

(10) Patent No.: US 6,889,560 B2
(45) Date of Patent: May 10, 2005

(54) NONINVASIVE CHARACTERIZATION OF A FLOWING MULTIPHASE FLUID USING ULTRASONIC INTERFEROMETRY

(75) Inventor: Dipen N. Sinha, Los Alamos, NM (US)

(73) Assignee: The Regents of the University of California, Los Alamos, NM (US)

( * ) Notice: Subject to any disclaimer, the term of this patent is extended or adjusted under 35 U.S.C. 154(b) by 15 days.

(21) Appl. No.: 10/649,886

(22) Filed: Aug. 26, 2003

(65) Prior Publication Data

US 2004/0035190 A1 Feb. 26, 2004

Related U.S. Application Data

(62) Division of application No. 10/187,024, filed on Jun. 28, 2002, now Pat. No. 6,644,119.

(51) Int. Cl.[7] .................................................. G01F 1/66
(52) U.S. Cl. .................. 73/861.25; 73/61.49; 73/61.79; 73/579
(58) Field of Search ......................... 73/861.25, 61.49, 73/61.79, 64.53, 579, 597

(56) References Cited

U.S. PATENT DOCUMENTS

| | | | | |
|---|---|---|---|---|
| 4,333,353 A | * | 6/1982 | Baumoel | 73/861.25 |
| 4,391,149 A | * | 7/1983 | Herzl | 73/861.25 |
| 5,198,989 A | * | 3/1993 | Petroff | 702/48 |
| 5,359,541 A | * | 10/1994 | Pope et al. | 702/25 |
| 5,473,934 A | * | 12/1995 | Cobb | 73/61.49 |
| 5,524,475 A | * | 6/1996 | Kolpak et al. | 73/19.03 |
| 5,606,130 A | * | 2/1997 | Sinha et al. | 73/627 |
| 5,767,407 A | | 6/1998 | Sinha | |
| 5,886,262 A | | 3/1999 | Sinha | |
| 6,295,873 B1 | * | 10/2001 | Condreva | 73/597 |

OTHER PUBLICATIONS

F. Eggers et al., "Ultrasonic Relaxation Spectroscopy in Liquids," Naturwissenchaften 63, 280 (1976).
Dipen N. Sinha et al., "Noninvasive Determination of Sound Speed and Attenuation in Liquids," Experimental Methods in the Physical Sciences, vol. 39, 307, Academis Press (Sep. 2001).
Zhijing Wang et al., "Ultrasonic Velocities in Pure Hydrocarbons and Mixtures," J. Acoustical Society of America 89(6), 2725 (1991).
Z. Wang et al., "Wave Velocities in Hydrocarbon–Saturated Rocks: Experimental Results," Geophysics 55(6), 723–.

* cited by examiner

*Primary Examiner*—Hezron Williams
*Assistant Examiner*—Katina Wilson
(74) *Attorney, Agent, or Firm*—Samuel M. Freund; Samuel L. Borkowsky

(57) ABSTRACT

An apparatus for noninvasively monitoring the flow and/or the composition of a flowing liquid using ultrasound is described. The position of the resonance peaks for a fluid excited by a swept-frequency ultrasonic signal have been found to change frequency both in response to a change in composition and in response to a change in the flow velocity thereof. Additionally, the distance between successive resonance peaks does not change as a function of flow, but rather in response to a change in composition. Thus, a measurement of both parameters (resonance position and resonance spacing), once calibrated, permits the simultaneous determination of flow rate and composition using the apparatus and method of the present invention.

16 Claims, 8 Drawing Sheets

# NONINVASIVE CHARACTERIZATION OF A FLOWING MULTIPHASE FLUID USING ULTRASONIC INTERFEROMETRY

This is a Divisional of application Ser. No. 10/187,024, filed Jun. 28, 2002, now U.S. Pat. No. 6,644,119.

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to swept frequency acoustic interferometric (SFAI) determination of sound velocity and absorption in fluids and, more particularly, to the use of SFAI to noninvasively determine flow velocity and composition for flowing fluids.

BACKGROUND OF THE INVENTION

Swept frequency acoustic interferometry (SFAI) [1] is an adaptation of the techniques of ultrasonic interferometry developed several decades ago for determining sound velocity and absorption in liquids and gases. In the original technique, and also in more recent modifications of the technique [2], the transducers (sensors) were placed in direct contact with the fluid being tested. This restricted the use of this technique to highly specialized laboratory characterization of fluids. By contrast, the SFAI technique extends the capabilities of the ultrasonic interferometry technique significantly and allows the noninvasive determination of velocity and attenuation of sound in a fluid (liquid, gas, mixtures, emulsions, etc.,) inside sealed containers (pipes, tanks, chemical reactors, etc.) over a wide frequency range. In addition, if the container material properties (density and sound velocity) are known, the liquid density can be determined using the SFAI technique. It has also been shown that it is possible to uniquely identify various chemical compounds and their most significant precursors based on the physical parameters of sound: velocity, attenuation, frequency dependence of sound attenuation, and density [3].

Oil companies have recently shown interest in noninvasive techniques for characterizing oil flow in pipes from oil fields.

U.S. Pat. No. 5,606,130 [4] states that it is anticipated that the SFAI measurements described therein can be performed on flowing samples in pipes. However, no mention is made therein of how to perform such measurements.

Accordingly, it is an object of the present invention to provide an apparatus and method for determining the composition of flowing fluids.

Another object of the invention is to provide an apparatus and method for determining the flow rate of a fluid.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for monitoring the composition of a fluid flowing through a vessel hereof includes the steps of: applying a continuous periodic acoustical signal to the outside of the vessel such that the acoustical signal is transferred to the flowing fluid, thereby generating vibrational resonance features having a plurality of maxima and minima therein; detecting the vibrational features generated in the flowing liquid; sweeping the continuous periodic acoustical signal through a chosen frequency range which includes two chosen consecutive maxima among the vibrational resonance features; and measuring the frequency difference between the two chosen consecutive maxima of the flowing fluid, whereby changes in the composition of the fluid are identified.

In another aspect of the present invention, in accordance with its objects and purposes, the method for monitoring the flow rate of a fluid through a vessel hereof includes the steps of: applying a continuous periodic acoustical signal to the outside of the vessel such that the acoustical signal is transferred to the flowing fluid, thereby generating vibrational resonance features having a plurality of maxima and minima therein; detecting the vibrational resonance features generated in the flowing liquid; sweeping the continuous periodic signal through a chosen frequency range which includes two chosen consecutive maxima in the standing-wave vibrational pattern; recording the frequency difference between the two chosen consecutive maxima to determine whether the composition of the fluid has changed; correcting the location of the resonance peaks in response thereto; and determining the frequency of one chosen resonance peak, whereby the flow rate of the fluid is determined.

In yet another aspect of the present invention, in accordance with its objects and purposes, the method for monitoring the composition of a fluid flowing at a flow rate through a vessel hereof includes the steps of: applying a continuous periodic acoustical signal to the outside of the vessel such that the acoustical signal is transferred to the flowing fluid, thereby generating vibrational resonance features having a plurality of maxima and minima therein; detecting the vibrational features generated in the flowing liquid; sweeping the continuous periodic acoustical signal through a chosen frequency range which includes one maximum among the vibrational resonance features; measuring the flow rate of the fluid; measuring the frequency of the maximum of the flowing fluid; and correcting the frequency of the maximum for the flow rate of the fluid, whereby changes in the composition of the fluid are identified.

In still another aspect of the present invention, in accordance with its objects and purposes, the method for monitoring the flow rate of a fluid having a composition and flowing through a vessel hereof includes the steps of: applying a continuous periodic acoustical signal to the outside of the vessel such that the acoustical signal is transferred to the flowing fluid, thereby generating vibrational resonance features having a plurality of maxima and minima therein; detecting the vibrational features generated in the flowing liquid; sweeping the continuous periodic acoustical signal through a chosen frequency range which includes one maximum among the vibrational resonance features; measuring the frequency of the maximum of the flowing fluid; determining the composition of the fluid; and correcting the frequency of the maximum for the composition of the fluid, whereby the flow rate of the fluid is determined.

Benefits and advantages of the present invention include the noninvasive measurement of flow rate and changes in composition of a flowing fluid.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Briefly, the present invention includes apparatus and method for noninvasively monitoring both the flow and/or the composition of a flowing fluid using ultrasound. In what follows, fluid will be defined as a liquid, including liquids with more than one constituent, liquids with some particulates and those containing gas bubbles. As will be described in detail hereinbelow, it was found that the position of the resonance peaks for a fluid excited by a swept-frequency ultrasonic signal change frequency both in response to a change in composition and in response to a change in the flow velocity thereof. Additionally, the frequency difference between successive resonance peaks does not change as a function of flow, but rather in response to a change in composition. Thus, a measurement of both parameters (resonance position and resonance spacing), once calibrated, permits the simultaneous determination of flow rate and composition using the apparatus and method of the present invention. Additional parameters useful for determining the fluid composition include the full-width-at-half-maximum of a resonance feature, the amplitude ratio and the acoustic impedance of the liquid. None of these parameters was found to change significantly as a function of flow rate. The apparatus was tested using decane, dodecane, water, and brine solutions to determine whether these compositions are readily distinguishable using the swept frequency acoustic interferometry (SFAI) technique that has been described in detail for static fluids in U.S. Pat. No. 5,767,407 [1] and U.S. Pat. No. 5,886,262 [5], the teachings of both references being hereby incorporated by reference herein.

Figure 1A:
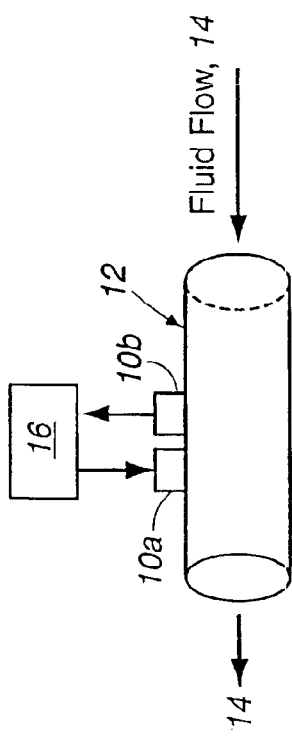
FIG. 1a is a schematic representation of one embodiment of the apparatus of the present invention showing a dual-element transducer located on one side of the pipe or tube through which the liquid flows.
Figure 1C:
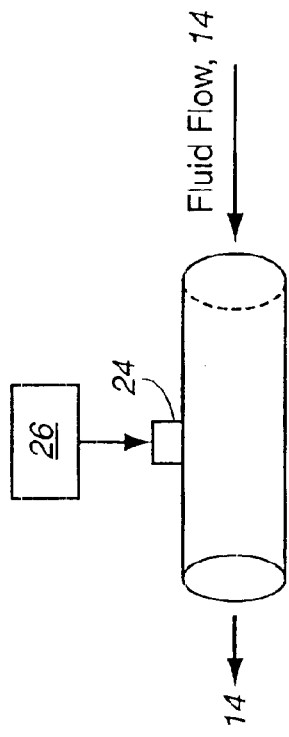
FIG. 1c shows a third embodiment of the present invention, wherein a single piezoelectric transducer is used for both generating an oscillatory signal in the sample and for responding to the resonances produced thereby.
Figure 1B:
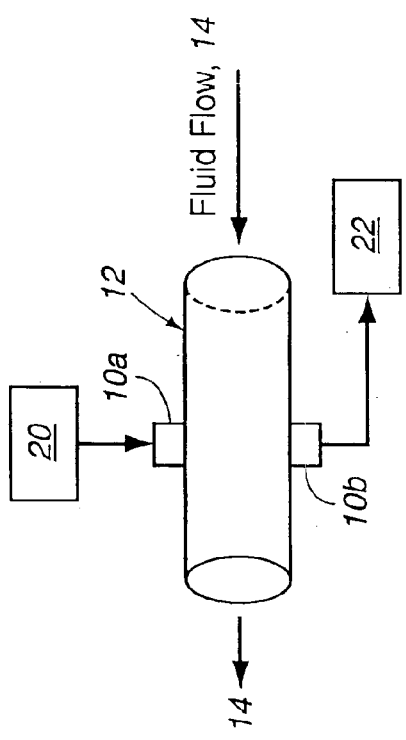
FIG. 1b shows a second embodiment of the apparatus of the present invention showing the transmitting transducer on one side of the pipe or tube and the receiving transducer on the other side thereof.

Reference will now be made in detail to the present preferred embodiments of the invention, examples of which are illustrated in the accompanying drawings. Similar or identical structure is labeled using identical callouts. Turning now to FIG. 1a, a schematic representation of one embodiment of the apparatus of the present invention is shown illustrating a dual-element transducer or two, single-element transducers 10a and 10b, located on one side of the pipe or tube, 12, through which fluid, 14, flows, and electronics, 16, provide the fixed or variable acoustic driving frequency, and receive the resonance signal generated in fluid 14. FIG. 1b shows a second embodiment of the apparatus of the present invention showing transmitting transducer 10a powered by swept sine-wave generator, 20, on one side of pipe or tube 12 and receiving transducer 10b in electrical connection with receiving and analyzing electronics, 22, on the other side thereof. Examples of the circuitry and principles of operation are found in the description for the '262 patent, supra. For single-frequency excitation of resonances within the fluid 14, the change in phase can be monitored by the apparatus. As will be demonstrated hereinbelow, tube or pipe 12 can be fabricated from metals, plastics or glass. FIG. 1c shows a third embodiment of the present invention, wherein a single piezoelectric transducer, 24, is used for both generating an oscillatory signal in the sample and for responding to the resonances produced thereby. As is also described in the description for the '262 patent, supra, bridge circuit, 26, is employed to derive a differential signal and includes one arm which contains transducer 24, a balancing arm which contains a matching or equivalent circuit for the transducer, and a swept sine-wave generator. When the transducer is not attached to the pipe, the output is zero; however, when attached to the pipe, a changing pipe impedance due to standing waves generated therein generates a signal of one arm relative to that of the other arm and the output is the difference between these values.

For measurement of the flow rate, it is necessary to correct for changes in the composition of the fluid, or at least have the knowledge that the composition is not changing. There are numerous commercially available composition monitoring devices including real-time, on-line devices such as infrared spectrometers, and uv/vis spectrometers, as examples, and sampling devices such as liquid chromatographs and mass spectrometers as examples. One might take a sample for analysis using a syringe introduced through a septum for off-site analysis. Another procedure would be to stop the flow and utilize the SFAI procedure detailed in Reference 1. Due to the number and variety of these methods, FIGS. 1a–1c do not show any devices for monitoring the composition of the flowing fluid; except for those taught by the present claimed invention. Similarly, for monitoring the composition of the fluid; certain embodi ments of the present invention require that a correction to the resonance peak location for the fluid flow rate be made, or at least knowledge that the flow rate is constant. There are numerous and varied commercially available flow measuring devices, some disposed in the interior of a pipe through which the fluid is flowing, and others disposed on the exterior of the pipe. Again, no flow measuring devices are illustrated in FIGS. 1a–1c except for those taught by the present claimed invention, for the same reason as the fluid composition monitoring apparatus is not displayed.

Figure 2:
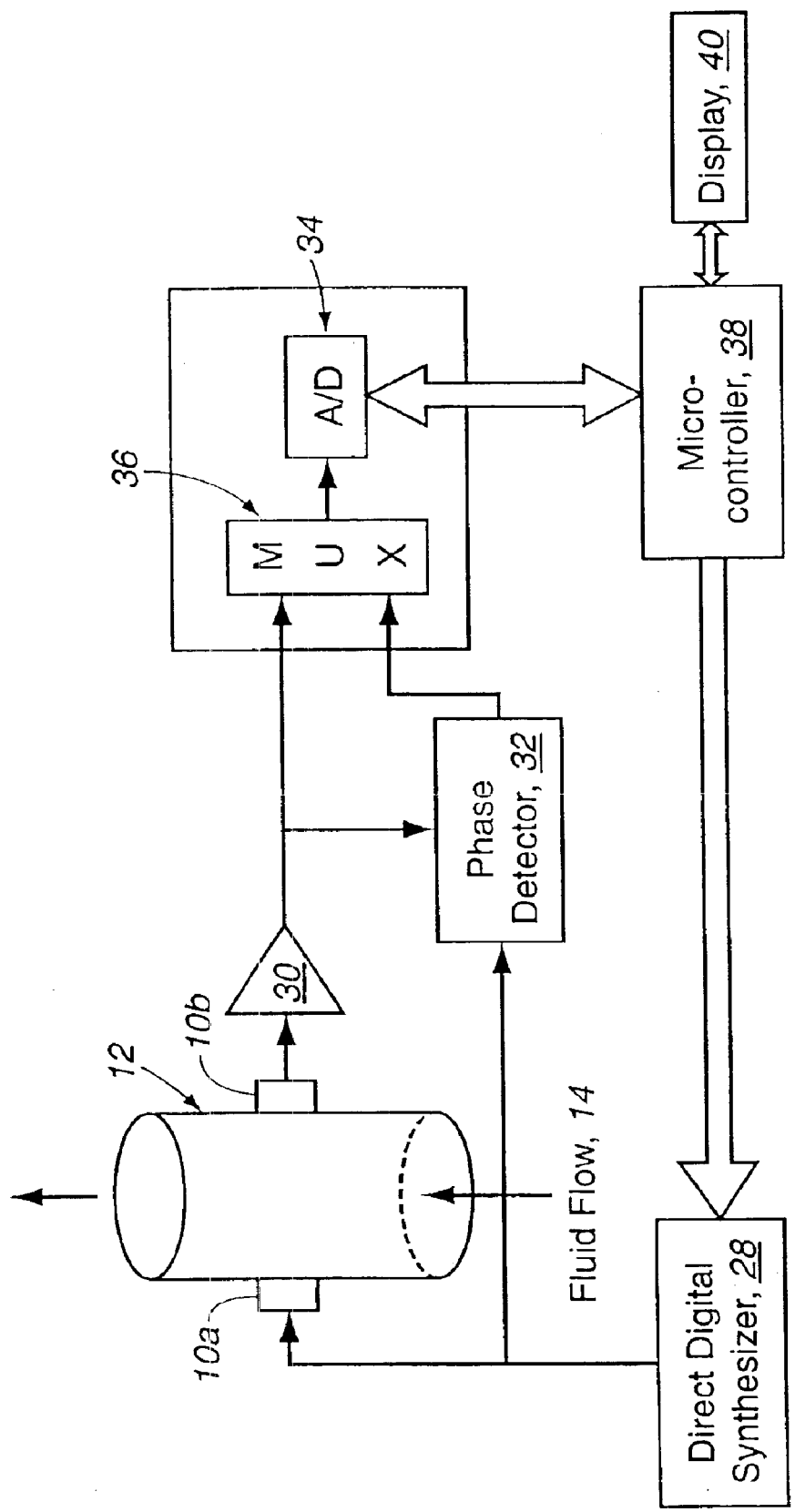
FIG. 2 shows an example of an electronic circuit suitable for observing the resonance response of the fluid flowing through the tube or pipe as a function of frequency; a similar apparatus would be suitable for observing changes in the phase of the fluid from that of the initial ultrasound signal impressed upon the tube or pipe by the transmitting transducer as a function of changes in fluid composition or flow rate.

FIG. 2 shows an example of an electronic circuit suitable for observing the resonance response of the fluid flowing 14 through the tube or pipe 12 as a function of frequency; a similar apparatus would be suitable for observing changes in the phase of the fluid from that of the initial ultrasound signal impressed upon the tube or pipe by the transmitting transducer as a function of changes in composition of the fluid and/or changes in fluid flow rate. The electronic circuit comprises a direct digital synthesizer (DDS) IC, 28, for generating frequencies up to 10 MHz; amplifier, 30, for amplifying the output signal of transducer 10b; phase detector, 32, for providing a voltage output proportional to the difference in phase between two sine-waves; analog-to-digital (A/D) converter, 34, having a minimum of two-channel multiplexing capability, 36 MUX (multiplexer); microcontroller, 38 having floating point calculation and fast Fourier transform (FFT) capability; and display unit, 40, for displaying the results. The two transducers utilized were commercial, off-the-shelf piezoelectric transducers (Panametric Videoscan 5 MHz center frequency, 0.5 in. diameter transducers). The actual brand is not critical to the measurements and almost any transducer can be employed.

Microcontroller 38 is software programmable and controls DDS 28 to generate sine-waves having a chosen frequency within the frequency range of the device. The frequency output of DDS 28 can either be fixed or varied with time (that is, swept). The frequency resolution of the apparatus used to demonstrate the present invention was better than 0.1 Hz. The frequency could be swept over a chosen frequency range in a fraction of a second.

The output of the DDS is used to excite the transmitter transducer 10a placed in physical contact with pipe 10 through which liquid 14 can be flowing. Second transducer 10b is used as the receiver. It is also possible to use a single transducer and measure the impedance change thereof (FIG. 1c hereof) to make the same type of measurement. However, for the present description, it is simpler to discuss the two separated transducer embodiment which are placed in physical contact with pipe 12 either on the same side thereof in the vicinity of one another or on opposite sides of pipe 12. Receiver transducer 10b receives the signal response of the fluid/pipe to the excitation signal from transducer 10a which is amplified by amplifier 30 with a gain of up to 60 dB. The amplified signal is processed using multiplexing input 36 of A-D converter 34. Microcontroller 38 controls the switching of multiplexer 36 input and the data output from A-D converter 34.

For phase measurements, phase detector 32 circuit is employed having as its output the phase difference between the signal to transmitter transducer 10a and the amplified signal of receiver transducer 10b. Typically, phase measurements are made at a fixed frequency that corresponds to a resonance peak when there is no liquid flow through the pipe. When the liquid is allowed to flow, the phase detector output is related to the magnitude of the flow. There is no simple relationship to describe the phase difference as a function of flow and a calibration is required. The observed phase difference is an approximately linear function of the flow (see FIG. 7 hereof. Microcontroller 38 can continuously monitor the phase output and convert this to a flow value and display the results using display 40.

For fluid composition monitoring, the circuit switches to the channel that directs the amplified receiver transducer signal output to A/D converter 34. For this measurement, the frequency applied to the transmitter transducer is rapidly swept through a chosen frequency range. This range depends on the dimensions of the pipe (see FIG. 3 hereof). Although any convenient frequency range may be employed, it is preferred that a frequency range between two successive wall resonances (see FIG. 3 hereof) be used. This produces a flat baseline and the results can be fitted to a theory involving simple equations. A brief description of the relationships follows.

As stated hereinabove, in order to readily obtain the acoustical properties of a fluid, it is convenient to select a measurement frequency range to avoid resonance contributions from the walls (approximately 4, 6, and 8 MHz in FIG. 3 as examples). To first order, this reduces the analysis essentially to that of sound transmission through a one-layer model making the calculations more straightforward without introducing substantial errors in the measurement of sound speed and sound attenuation. This is similar to avoiding the transducer crystal resonance frequency region in traditional interferometry. The intensity transmission coefficient, T, for the case of a single fluid layer having path-length, L, attenuation coefficient, $\alpha_L$ ($\alpha_L L \ll 1$), and sound speed, $c_L$, between two identical wall boundaries can be expressed as $$T = \frac{1}{\left(1 + \frac{1}{2}\sigma\alpha_L L\right)^2 + \frac{\sigma^2 - 4}{4}\sin^2\left(\frac{\omega}{c_L}L\right)}, \quad (1)$$

where, $\sigma = z_w/z_L + z_L/z_w$, $\omega = 2\pi f$, is the angular frequency, and $z_w$ and $z_L$ are the acoustic impedance of the wall and fluid, respectively. For most liquids inside a metal container, $\sigma \approx z_w/z_L$. T in Eq. (1) is a periodic function of $\omega L/c_L$ and reaches a maximum (peak) value whenever the condition $2\pi f_n L/c_L = n\pi$ is satisfied, where $f_n$ is the frequency of the n-the peak. From this condition, the sound speed $c_L$ ($c_L = 2 L \Delta f$) can be determined if the frequency difference between successive peaks is measured.

As stated, the sound speed in the fluid is determined from the frequency spacing between any two consecutive peaks. Therefore, one needs to sweep the frequency over a range that encompasses any two successive resonance peaks. The digitized data of two resonance peaks can then be used to extract the sound speed since the liquid path length (the diameter of the pipe) is known. This is the most expedient manner for determining the sound speed in the fluid, and the measurement can be made in a fraction of a second. If either greater accuracy or resolution is required, a second approach may be used. In this approach, a much larger frequency range is covered such that multiple resonance peaks (say, 10) are observed. The microcontroller is used to perform a FFT of the data which determines the periodicity of the resonance peaks which is directly related to the peak spacing. This is equivalent to averaging the sound speed measurement over multiple peak spacings.

Sound attenuation and liquid density are related to the frequency spectrum. The ratio of transmission coefficient minima, $T_{min}$, and maxima, $T_{max}$, can be expressed in terms of $\sigma$ and $\alpha_L$ as:

$$\frac{T_{\min}}{T_{\max}} = \frac{2}{\sigma} + L\alpha_L(f^2). \quad (2)$$

Equation (2) illustrates that both $\alpha_L$ and $\sigma$ can be determined from a linear fit of the data of the transmission ratio factor as a function of $f^2$. The intercept at zero frequency is related to the acoustic impedance ratio $\sigma$. If the impedance of the wall material is known, the liquid density can be determined since the sound speed of the fluid is independently determined as discussed hereinabove.

Another for determining the sound attenuation coefficient is to utilize the half-power bandwidth of observed resonance peaks. From Eq. (1), an inverse solution for the half-power bandwidth, $\delta f$, can be derived in terms of acoustic properties of the fluid according to $$\delta f = \frac{2c_L}{\pi \sigma L} + \frac{c_L \alpha_L(f^2)}{\pi}. \quad (3)$$

Figure 8:
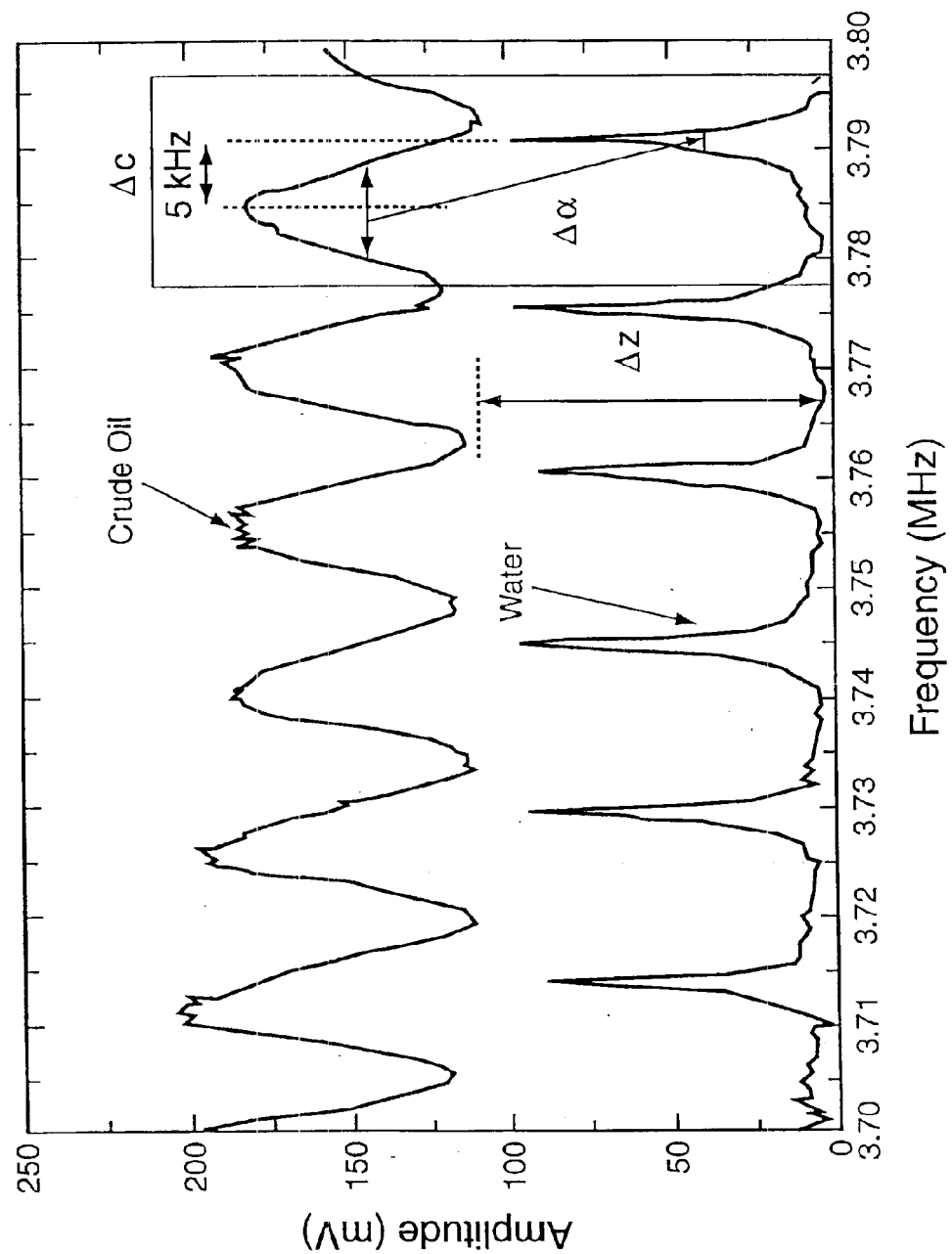
FIG. 8 shows the resonance patterns for water and oil as a function of frequency and illustrates that at an appropriate frequency the resonance peak characteristics are sensitive to the acoustic properties of the liquid.

Similar to Eq. (2), the second term is the contribution from liquid sound absorption and is identical to the solution obtained from resonator theory of transducers in direct contact with the liquid. The first term, the width extrapolated to zero frequency $\delta f_0$, is independent of frequency and depends on $\sigma$, $c_L$, and L. This term results from the reflection loss at the wall-liquid interface due to acoustic impedance mismatch and can be used to determine liquid density if the acoustic impedance of the wall is known. This analysis can be used to extract the absolute value of the sound absorption of the liquid. More often, monitoring the peak width for the resonance peaks for say oil and water (see FIG. 8 hereof) to obtain qualitative discrimination is sufficient. The resonance width is the full-width-at-half-maximum of the peak, and the microcontroller can rapidly calculate this quantity by fitting the top part of any peak with a Lorentzian line shape. The Lorentzian can be linearized by inverting (taking the reciprocal of the amplitude at each frequency) the data and then a simple parabolic fit is all that is necessary instead of a nonlinear least-squares fitting. The width indicated for crude oil in FIG. 8 is meant only for qualitative description.

Thus, the spectrum contains all the information related to the liquid, any desired parameter can be extracted through simple calculations.

The above description covers the behavior of sound transmission through a fluid path as a function of frequency and Eq. (1) described the frequency spectrum. It is possible to least-squares curve-fit this equation to observed experimental data to extract various parameters of the fluid, such as sound speed, sound absorption, and density. However, it is also possible to derive the same information with good accuracy even by monitoring a single resonance peak. In practice, one often requires to monitor the change in the quality of the fluid, in terms of sound speed, sound absorption and density variation, flowing through a pipe and not absolute values of these quantities. In such a situation, an electronic circuit simply selects and tracks a single resonance peak and measures the peak width, peak position, and the minimum value (the baseline) of the resonance curve.

If the sound speed of the fluid changes, the selected resonance peak position will change in frequency. This frequency shift ($\Delta f_s$) is related to the sound speed variation ($\Delta c$) simply as $\Delta f_s=(n/2L) \Delta c$. Here n, is the order number of the particular resonance is peak. Similarly, if the sound absorption of the liquid changes then the observed difference in full-width at half-maximum ($\delta f$) value of the resonance peak for a selected resonance peak $\Delta(\delta f)$ provides the change in sound absorption as $\Delta (\delta f) \approx (\Delta c/\pi)\Delta \alpha$. Another method for determining the change in sound absorption is to measure the ratio of the resonance peak minimum, $T_{min}$ to the peak maximum, $T_{max}$ for a single resonance feature. The change in absorption $\Delta\alpha=\Delta(T_{min}/T_{max})/L$ (see Eq. (2) and FIG. 8 hereof. This approach provides a more rapid procedure for determining $\Delta\alpha$ and does not require curve fitting.

Finally, the variation in the minimum ($T_{min}$) of the resonance curve can provide a measure of the variation in the change in acoustic impedance of the liquid. The relationship between the two parameters can be expressed as $\Delta T_{min}=(2/Z_w) \Delta Z$, where $\Delta Z$ is the change in acoustic impedance of the liquid. All these relationships are derived from Eq. (1), and are shown graphically in FIG. 8 hereof for description purposes. For qualitative monitoring of variation in sound absorption, for example, for simple discrimination between oil and water, it is expedient to simply determine the width of the resonance peak between the maximum and minimum of the resonance as shown in FIG. 8. For accurate determination of sound absorption, it is better to fit the resonance spectrum with several peaks using Eq. (1).

By employing a phase-locked-loop circuit that simultaneously monitors both the resonance peak position of a single peak and the peak width in the most sensitive frequency region, both sound speed and sound attenuation are provided continuously. These values are then used to characterize the fluid as in the case of the SFAI. With an additional circuit, the density of the liquid can be monitored. The phase-locking is accomplished by using a saw-tooth wave signal to vary the frequency of the excitation transducer around the desired resonance frequency of a single resonance peak. The resonance peak is monitored as a function of time and provides a measure of the sound speed because the pipe diameter is known. In this case, it is not necessary to determine the frequency spacing between any two consecutive peaks because the resonance spectrum is determined by the path length (pipe or tube diameter) and the sound speed of the liquid. Therefore, the position of a single known peak determines the sound speed. The output of the frequency modulation is a signal that is amplitude modulated as it is swept through a resonance peak. If the resonance is sharp then the amplitude modulation over the short frequency sweep region is of high amplitude with a high median amplitude value. For low amplitude or wide resonance peaks, the output signal is of lower median value with lower amplitude excursions. Therefore, by measuring the RMS value of the signal and AC coupling it so that the DC median value is filtered out, it is possible to derive the resonance peak width. The median DC value provides a measure of the liquid density.

Figure 3:
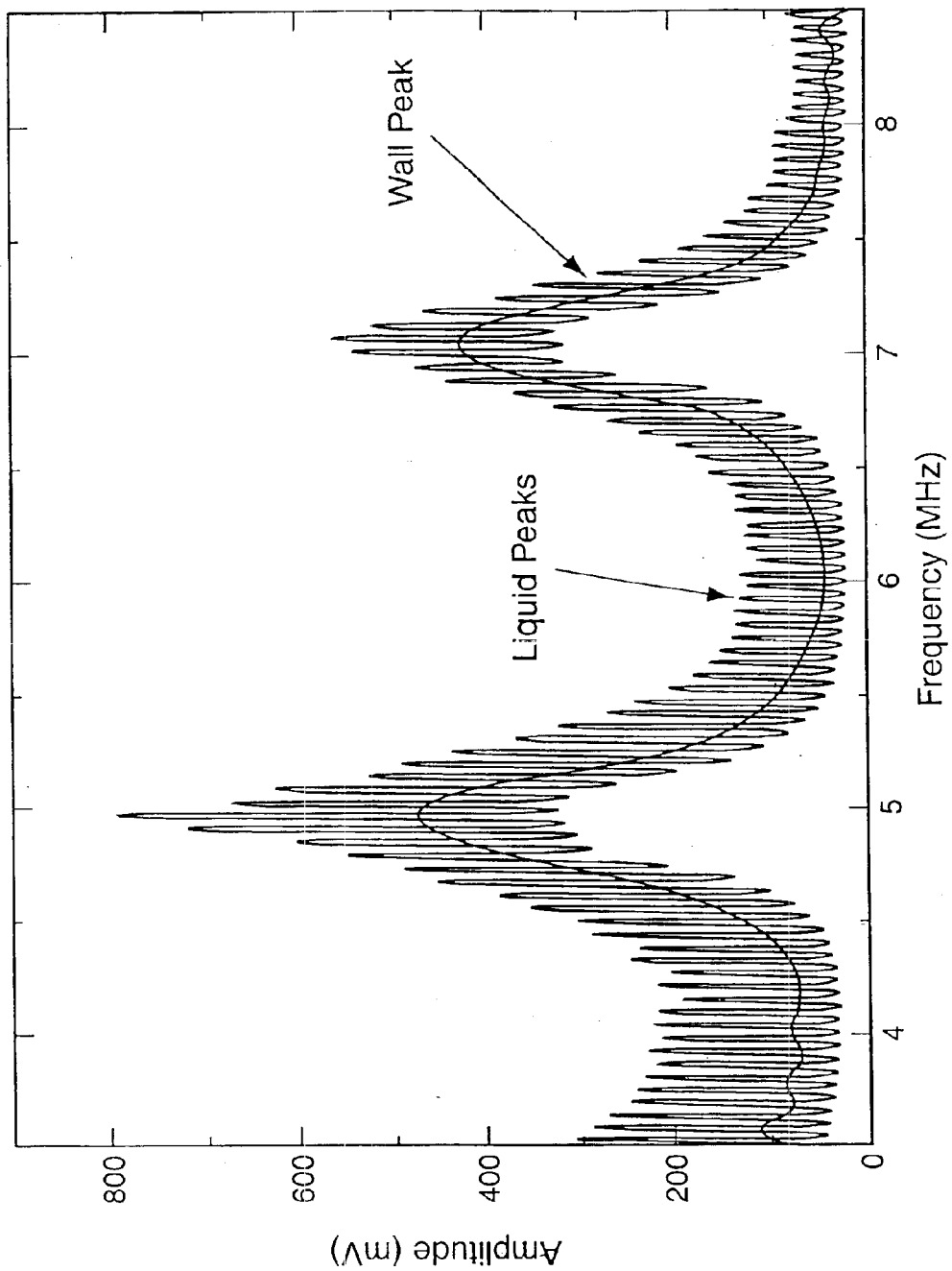
FIG. 3 is a composite resonance spectrum for a noninvasive measurement using a swept frequency apparatus and method of the present invention, and illustrates that liquid peaks can be studied independently of the resonances induced in the wall of the container if an appropriate frequency region is selected.

FIG. 3 is a composite resonance spectrum for a noninvasive measurement using the swept frequency apparatus and method of the present invention on a container having a finite wall thickness, and illustrates that liquid peaks can be studied independently of the resonances induced in the wall of the container if an appropriate frequency region is selected. The following graph shows what a typical spectrum looks like when a swept frequency measurement is made from outside a container with a finite wall thickness.

Figure 4:
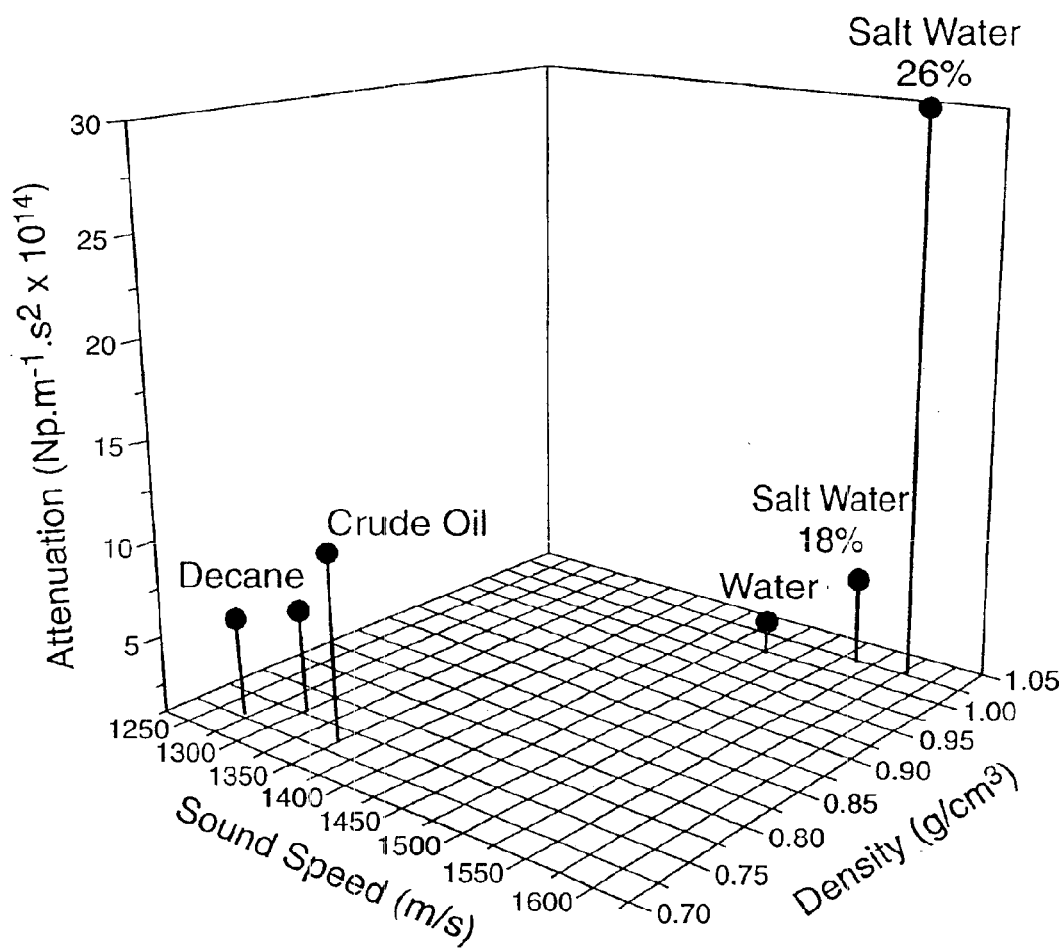
FIG. 4 is a graph of the physical properties of several liquids measured in a static container.

FIG. 4 is a graph of the physical properties of several liquids measured in a static container. Decane and dodecane were investigated since both of these liquids are known to have similar properties to those for oil. Acoustically, these liquids are far apart. The sound speed and attenuation values are summarized in the TABLE.

TABLE

| Liquid | Sound speed m/s | Density g/cm$^3$ | Attenuation Np m$^{-1}$ s$^2$ × 10$^{14}$ |
|---|---|---|---|
| Decane | 1263 | 0.73 | 5.7 |
| Dodecane | 1300 | 0.75 | 6.3 |
| Water | 1483 | 1.00 | 2.5 |
| Water + 18% (NaCl) | 1550 | 1.01 | 6.0 |
| Water + 26% (NaCl) | 1585 | 1.02 | 30.0 |

The resolution for sound speed for the SFAI technique of the present invention is approximately ±2 m/s; this can be improved to 0.1 m/s, if necessary. This difference between decane and dodecane permits them to be identified. Differentiating between water, brine and decane (or dodecane) is straightforward. The same data are presented in a 3-dimensional graph in FIG. 4 for clarity.

Recent studies on the sound speed in pure hydrocarbons and mixtures using the traditional pulse-echo technique by Wang and Nur [5] show that sound speed in 13 n-alkanes, 10 1-alkenes, and 3 napthene hydrocarbon samples show that the sound speed decreases linearly with temperature with slopes ranging from −3.43 to −4.85 [m/s]/° C. in a temperature range between −12° to 132° C. Therefore, if the temperature is known, the sound speed can be corrected for temperature. In a separate study [6] it is shown that the sound speed c for hydrocarbons can be expressed as a function of temperature T and molecular weight M in atomic mass units as:

$$c = c_0 - \left(0.306 - \frac{7.6}{M}\right)T$$

where, $c_0$ is a constant. This shows that it should be possible to identify various hydrocarbons using sound speed if this quantity can be measured accurately.

In addition to sound speed, the SFAI technique can also determine sound absorption in the fluids, which provides an additional physical parameter for oil characterization. Hydrocarbons also show pronounced frequency dependent sound absorption. The SFAI technique of the present invention is capable of this type of measurement as well.

Figure 5:
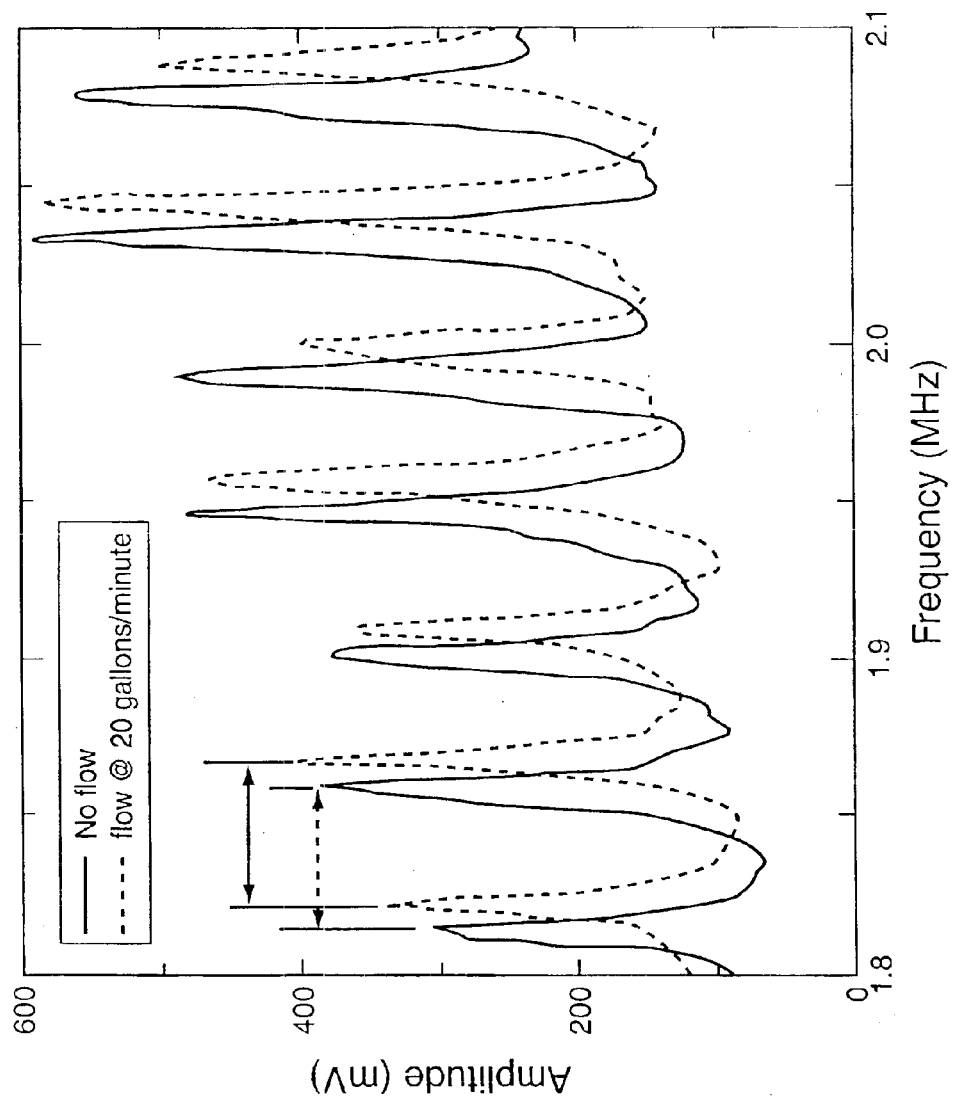
FIG. 5 shows swept frequency acoustic interferometry measurements made under flowing conditions, showing that the sound speed which is related to the spacing between the peaks for consecutive resonance does not change as a result of the flow, nor does the sound attenuation which is related to the width of the resonance peaks.

A flow loop was employed to perform SFAI measurements under flowing conditions. A 4.5-in. diameter plastic tube was used in the flow loop. Water was used for the liquid because it is easier to work with than crude oil. The measurement was also performed with vegetable oil. FIG. 5 shows the measurements under flowing conditions between 0 and 20 gal./min. of water. The spacing between consecutive resonance peaks is seen to be the same for flowing and non-flowing water. This indicates that the sound speed does not change when the liquid is flowing. The width of the resonance peaks are also observed to be the same, indicating that sound attenuation also remains invariable under flowing conditions. The difference between the two spectra is a slight shift of the entire pattern in frequency.

It is believed by the present inventor that the frequency shift is due to a slight variation in the acoustical properties of the fluid due to the flow boundary layer formed adjacent to the inner surface of the wall. This boundary layer tends to introduce a phase shift of the sound waves reflecting from the wall which can affect the standing-wave pattern formed inside the total fluid path length. The baseline drift to higher amplitude toward the higher frequency side of the figure is a result of the fact that the data presented are somewhat close to a wall resonance peak (see FIG. 3 hereof. It has been observed that the constancy of the sound speed is observed from the FFT of the data.

Figure 6:
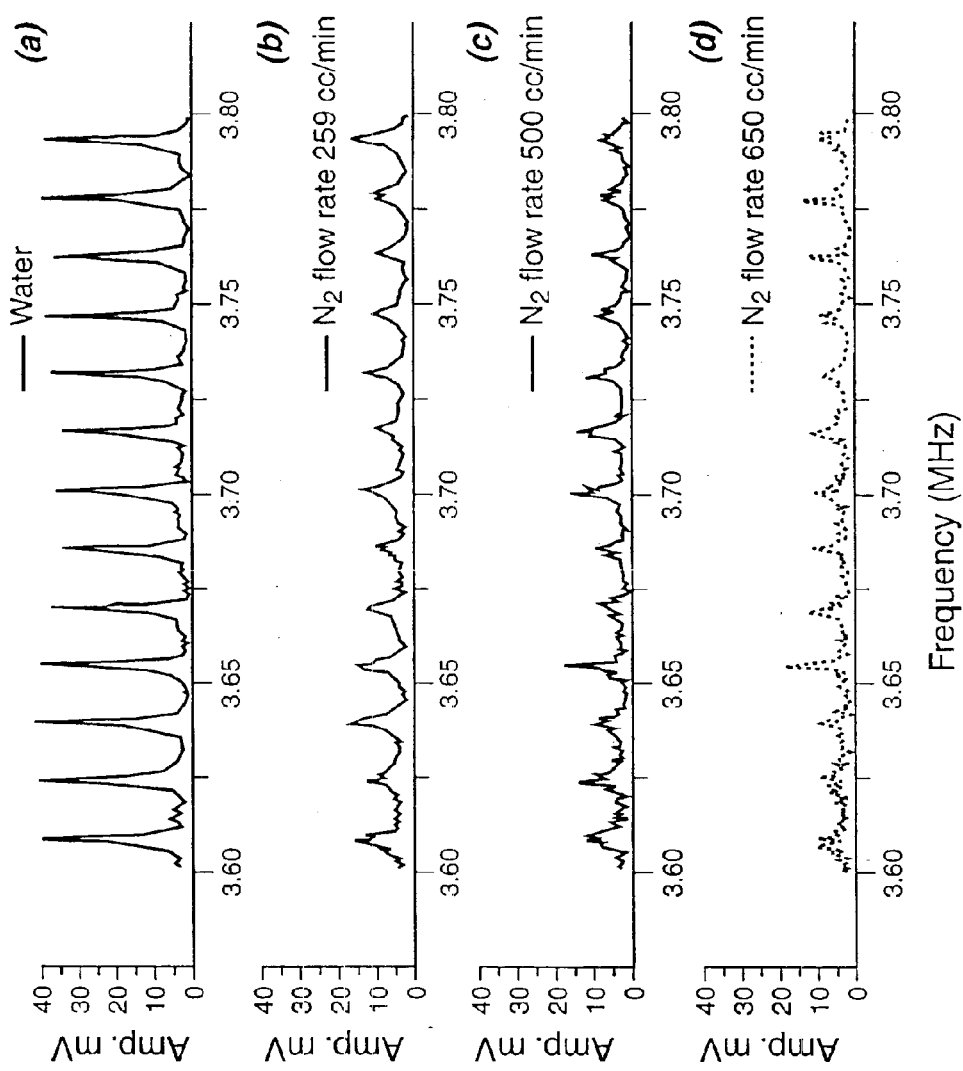
FIG. 6 shows swept frequency acoustic interferometry measurements made in a liquid which contains bubbles; again, the spacing between the peaks does not change.

FIG. 6 shows that SFAI measurements required for determining sound speed can be made with fluids containing bubbles of gas. For this measurement, nitrogen gas was bubbled through the bottom of a Plexiglas tube about 2-in. in diameter, and the measurements were made by attaching two transducers on the outside of the tube. To be noted is that that the frequency spacing between consecutive resonance peaks does not significantly change, and that the spectra can be clearly observed (the measurements were made with little (~1 ms) integration time); moreover, the periodicity can still be determined at relatively high bubbling rates. This indicates that the sound speed does not change appreciably until the volume fraction of bubbles is large when the bubbling rate is too high. If the integration of the measurement is increased by a factor of 10, the signal-to-noise ratio of the data was found to improve considerably, and the observed pattern for the bubbling liquid was found to be similar to the same liquid without introduced bubbles. This is because all the fluctuations due to the bubbles in the measurements are averaged out, and up to a certain bubble rate, the SFAI measurements are still quite reliable.

Figure 7:
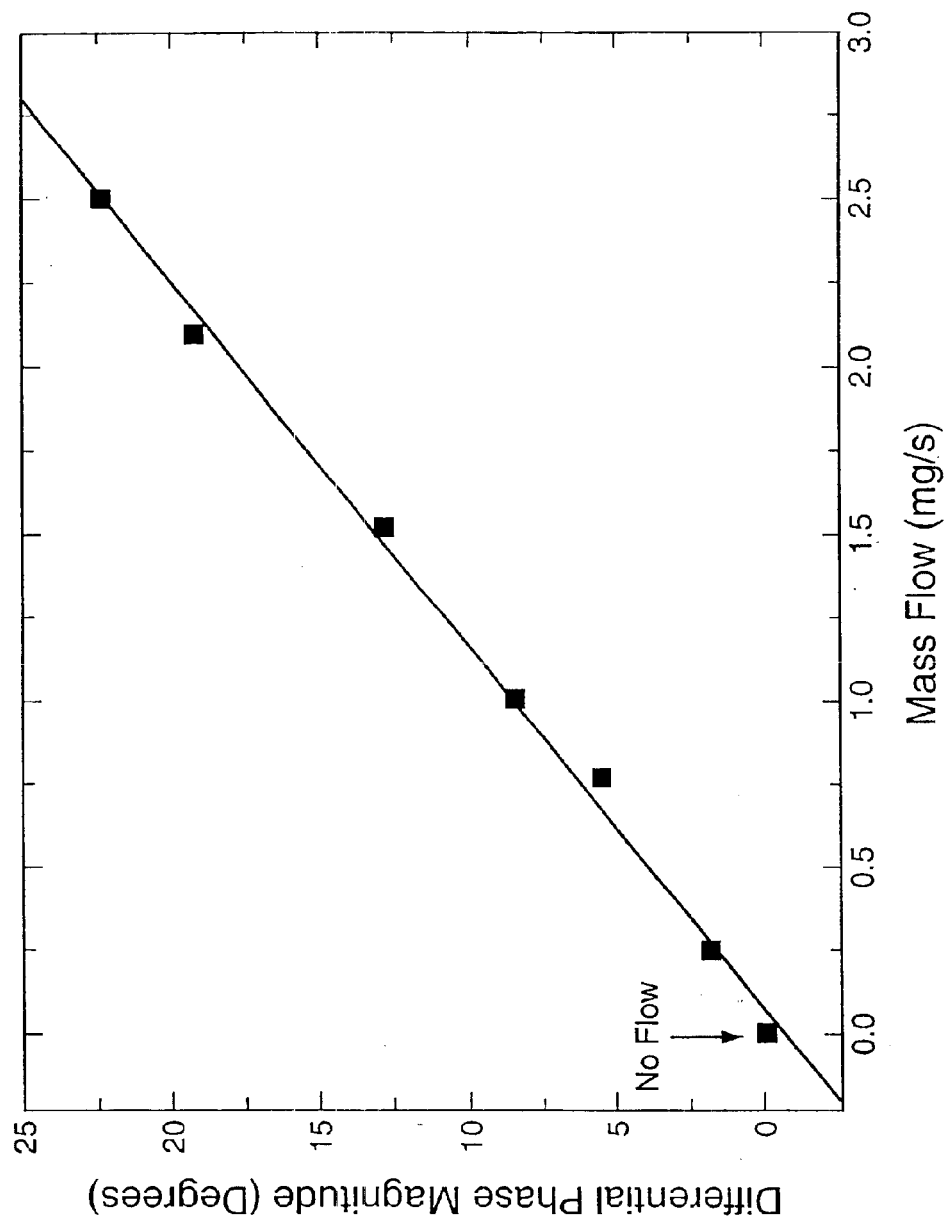
FIG. 7 is a graph of the measured differential phase magnitude as a function of mass flow for water.

FIG. 7 is a plot of the shift in phase angle as a function of mass flow, demonstrating that the apparatus of the present invention is useful as a noninvasive flow meter; that is, by attaching transducers to the outside of an existing pipe, the flow of the fluid therein can be monitored.

For real-time (continuous) monitoring, it has been found to be most useful to select a single resonance peak at an appropriate frequency. FIG. 8 is a plot of resonance amplitude as a function of frequency for crude oil (upper trace) and for water (lower trace) in a 2-inch diameter glass pipe. In the frequency range between 3.78 and 3.8 MHz (enclosed by the rectangle), the particular resonator cavity (the inside of the pipe) reaches its maximum sensitivity in terms of monitoring changes in sound speed. There are many such frequencies dispersed in a regular manner. A frequency shift of 5 kHz is observed between the data for crude oil and water. The SFAI technique of the present invention can easily resolve 1 Hz, therefore, allowing a sound speed resolution of 1 part in 5000. Besides the shift in frequency, the resonance width also changes dramatically which indicates a large variation in sound absorption. In addition, the minimum of the resonance also changes due to a change in acoustic impedance mismatch and can be related to liquid density. Electronic circuitry has been developed that can monitor all three parameters in a continuous manner. The shift in the baseline for the two plots (water and crude oil) is due to the fact that the acoustic impedance is different for the two fluids. The minimum value of the resonance provides a measure of the fluid density that can be derived from the acoustic impedance mismatch between the pipe wall and the fluid inside.

Thus, it is seen that frequency location of the resonance peaks varies as a function of both the composition of the fluid and its flow rate. If a flow meter is desired, the composition must be determined to be constant; this can be achieved by monitoring the peak spacing to determine that the sound speed of the fluid remains relatively constant for in-situ calibration. The calibration can also be performed using a small section of the same pipe and a known liquid elsewhere in any flowing system to derive the calibration information. In the flow calibration, any resonance peak in a desired frequency range (preferably in the frequency range in the middle of two wall resonance peaks) is monitored as a function of the liquid flow. The wall resonance peak positions are determined by the wall thickness. The present apparatus can be calibrated for both high and low sensitivity measurements as follows: For low frequencies (approximately 1 MHz), the shift of the resonance peaks is smaller than the shift observed at much higher frequency (approximately 10 MHz). By observing multiple frequency ranges, it is possible to obtain different levels of sensitivity. This calibration process is no different than for other transit-time ultrasonic flow meters where the fluid sound speed is to be determined. Once the apparatus is calibrated for flow, then both sound speed (and sound absorption) and fluid flow can be simultaneously monitored if great accuracy in the measurement is not desired. For many practical applications, such as flow and composition monitoring in the oil (petroleum products) industry, an oil flow calibration provides adequate accuracy. It is also possible, in principle, to extend the flow calibration from one liquid, for example, water to oil. FIG. 8 illustrates the difference in the resonance peaks for oil and water. The widths of the resonance peaks are different for the two liquids, and each liquid can be identified based on the resonance characteristics of just a single resonance peak. Therefore, once the calibration for flow is completed for oil and separately for water, it is possible to extrapolate the flow rate when the flowing fluid is a combination of the two liquids because this quantity is intermediate between the two calibrations. This is possible because the composition can be monitored from a measurement of the peak spacing or by FFT of the resonance data, whereas the flow is measured by tracking the position of a single resonance peak. These two measurements are independent of each other to a large extent in practice.

The present invention provides information at both low and high flow rates. Since the frequency shift of the peaks due to flow increases with frequency, for low flow rates it is convenient to use a higher frequency range ($\geq 5$ MHz) where a small flow rate produces a measurable shift in peak frequency or phase shift of any selected resonance peak. By contrast, for higher flow rates, the resonance peak shift can be large and one may lose track of the selected peak which is equivalent to exceeding a 360-degree phase shift. In this case, it is appropriate to observe the data at a lower frequency region ($\approx 1$ MHz). The appropriate frequency ranges depend on the particular pipe geometry and may be determined during the initial calibration process where a wideband frequency scan is employed to determine the characteristics of the pipe (see FIG. 3 hereof). As mentioned hereinabove, it is preferable to use the frequency regions between two wall resonance frequencies for both flow and composition monitoring.

For a calibration of the system for flow, measurements (receiver signal amplitude and phase difference) are made with a flowing liquid for several flow values and the entire frequency spectrum is monitored. Once this is done, the calibration information for the low and high frequency ranges are extracted from these spectra and stored in the microcontroller as terms of simple equations. From this any value can then be interpolated for actual measurement.

Once the apparatus is calibrated for flow, both sound speed (and sound absorption) and fluid flow can be simultaneously monitored if great accuracy in the measurement is not desired. For flow and composition monitoring of petroleum products, a simple flow calibration with oil can provide adequate monitoring. It is also possible, in principle, to extend the flow calibration from one liquid, for example, water to oil. FIG. 8 shows the difference in the resonance peaks for oil and water, and the liquid can be readily identified from the resonance characteristics of a single peak. Once the calibration for flow is performed with oil and then with water, it is possible to correct the flow when the flowing fluid is a combination of any two because the measured results will be between those for either liquid. This is possible because the composition is monitored by measuring the peak spacing or FFT of the resonance data, whereas the flow is measured by tracking the position of a single resonance peak. These two measurements are independent of each other.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

REFERENCES

1. U.S. Pat. No. 5,767,407 for "Noninvasive Identification Of Fluids By Swept-Frequency Acoustic Interferometry," which issued to Dipen N. Sinha on Jun. 16, 1998.
2. F. Eggers and The. Funck, "Ultrasonic relaxation spectroscopy in liquids", *Naturwissenschaften* 63, 280 (1976).
3. Dipen N. Sinha and Greg Kaduchak, "Noninvasive Determination of Sound Speed and Attenuation in Liquids," Experimental Methods in the Physical Sciences, Volume 39, Academic Press (September 2001).
4. U.S. Pat. No. 5,606,130 for "Method For Determining The Octane Rating Of Gasoline Samples By Observing Corresponding Acoustic Resonances Therein" which issued to Dipen N. Sinha and Brian W. Anthony on Feb. 25, 1997
5. U.S. Pat. No. 5,886,262 for "Apparatus And Method For Comparing Corresponding Acoustic Resonances in Liquids" which issued to Dipen N. Sinha on Mar. 23, 1999.
6. Zhijing Wang and Amos Nur, J. Acoust. Soc. Am. 89, 2725(1991).
7. Z. Wang and A. Nur, Geophysics 55, 723 (1990).

What is claimed is:

1. A method for monitoring the composition of a fluid flowing through a vessel which comprises the steps of:
   (a) applying a continuous periodic acoustical signal to the outside of the vessel such that the acoustical signal is transferred to the flowing fluid, thereby generating vibrational resonance features having a plurality of maxima and minima therein;
   (b) detecting the vibrational features generated in the flowing liquid;
   (c) sweeping the continuous periodic acoustical signal through a chosen frequency range which includes two chosen consecutive maxima among the vibrational resonance features; and
   (d) measuring the frequency difference between the two chosen consecutive maxima of the flowing fluid.

2. The method as described in claim 1, further comprising the step of determining the full-width-at-half-maximum of at least one of the two chosen consecutive resonance features.

3. The method as described in claim 1, further comprising the step of determining the acoustic impedance of the fluid.

4. The method as described in claim 1, further comprising the step of determining the ratio of the resonance feature minimum to the resonance feature maximum.

5. An apparatus for monitoring the composition of a fluid flowing through a vessel which comprises in combination:
   (a) a first transducer in acoustic contact with the outside surface of said vessel for applying a continuous periodic acoustical signal to the outside of said vessel such that the acoustical signal is transferred to said flowing fluid, thereby generating vibrational resonance features having a plurality of maxima and minima therein;
   (b) a second transducer in acoustic contact with the outside of said vessel and located on the side thereof opposite to said first transducer for detecting the vibrational resonance features generated in the flowing liquid;
   (c) a sweep generator for sweeping said first transducer through a chosen frequency range which includes two chosen consecutive maxima among the vibrational resonance features; and
   (d) a data processor for determining the frequency difference between the two chosen consecutive maxima of the flowing fluid.

6. The apparatus as described in claim 5, wherein said data processor determines the line width of at least one of the two chosen consecutive resonance features.

7. The apparatus as described in claim 5, wherein said data processor determines the acoustic impedance of the fluid.

8. The method as described in claim 5, wherein said data processor determines the ratio of the resonance feature minimum to the resonance feature maximum.

9. An apparatus for monitoring the composition of a fluid flowing through a vessel which comprises in combination:
   (a) a first transducer in acoustic contact with the outside surface of said pipe for applying a continuous periodic acoustical signal to the outside of said vessel such that the acoustical signal is transferred to said flowing fluid, thereby generating vibrational resonance features having a plurality of maxima and minima therein, and for detecting the generated vibrational resonance features;
   (b) a sweep generator for sweeping said first transducer through a chosen frequency range which includes two chosen consecutive maxima in the vibrational resonance features; and
   (c) a data processor for measuring the frequency difference between the two chosen consecutive maxima of the flowing fluid.

10. The apparatus as described in claim 9, wherein said data processor determines the line width of at least one of the two chosen consecutive resonance features.

11. The apparatus as described in claim 9, wherein said data processor determines the acoustic impedance of the fluid.

12. The apparatus as described in claim 9, wherein said data processor determines the ratio of the resonance feature minimum to the resonance feature maximum.

13. An apparatus for monitoring the composition of a fluid flowing through a vessel which comprises in combination:
   (a) a first transducer in acoustic contact with the outside surface of said vessel for applying a continuous periodic acoustical signal to the outside of said vessel such that the acoustical signal is transferred to said flowing fluid, thereby generating vibrational resonance features having a plurality of maxima and minima therein;
   (b) a second transducer in acoustic contact with the outside of said vessel and located on the same side thereof as said first transducer and in the vicinity thereof, for detecting the vibrational resonance features generated in the flowing liquid;
   (c) a sweep generator for sweeping said first transducer through a chosen frequency range which includes two chosen consecutive maxima among the vibrational resonance features; and
   (d) a data processor for determining the frequency difference between the two chosen consecutive maxima of the flowing fluid.

14. The apparatus as described in claim 13, wherein said data processor determines the line width of at least one of the two chosen consecutive resonance features.

15. The apparatus as described in claim 13, wherein said data processor determines the acoustic impedance of the fluid.

16. The apparatus as described in claim 13, wherein said data processor determines the ratio of the resonance feature minimum to the resonance feature maximum.

* * * * *